United States Patent [19]
Cullen et al.

[11] Patent Number: 5,965,445
[45] Date of Patent: Oct. 12, 1999

[54] POLYCYCLIC ETHER ANTIBIOTIC HAVING ANTHELMINTIC, ANTICOCCIDIAL AND GROWTH PROMOTANT ACTIVITY

[75] Inventors: Walter P. Cullen, East Lyme; John P. Dirlam, Gales Ferry, both of Conn.; Hiroshi Maeda, Chita-Gun; Junsuke Tone, Chita, both of Japan

[73] Assignee: Pfizer Inc., New York, N.Y.

[21] Appl. No.: 07/849,552

[22] Filed: Mar. 11, 1992

Related U.S. Application Data

[63] Continuation of application No. 07/527,627, May 23, 1990, Pat. No. 5,155,097.

[51] Int. Cl.⁶ ...................................................... C12N 1/00
[52] U.S. Cl. ......................... 435/886; 435/74; 435/119; 514/25; 514/27; 536/16.8; 536/18.1
[58] Field of Search .................................. 536/16.8, 18.1; 514/25, 27; 435/74, 119, 886

[56] References Cited

U.S. PATENT DOCUMENTS

| | | | |
|---|---|---|---|
| 4,022,885 | 5/1977 | Celmer et al. | 424/122 |
| 4,150,152 | 4/1979 | Celmer et al. | 424/122 |

*Primary Examiner*—Elli Peselev
*Attorney, Agent, or Firm*—Peter C. Richardson; Paul H. Ginsburg; Bryan C. Zielinski

[57] ABSTRACT

An acidic polycyclic ether antibiotic, having structure established by X-ray crystallography, is formed by fermentation of a novel microorganism, Streptomyces sp. ATCC 55028. This novel antibiotic is useful as an anticoccidial in chickens, in the prevention or treatment of swine dysentery, as a growth promotant in cattle and swine, and as an anthelmintic in mammals, particularly in dogs, cats, sheep, cattle and swine.

2 Claims, No Drawings

POLYCYCLIC ETHER ANTIBIOTIC HAVING ANTHELMINTIC, ANTICOCCIDIAL AND GROWTH PROMOTANT ACTIVITY

This is a continuation of application Ser. No. 07/527,627, filed on May 23, 1990 now U.S. Pat. No. 5,155,097.

BACKGROUND OF THE INVENTION

The present invention concerns a new acidic polycyclic ether antibiotic having the formula:

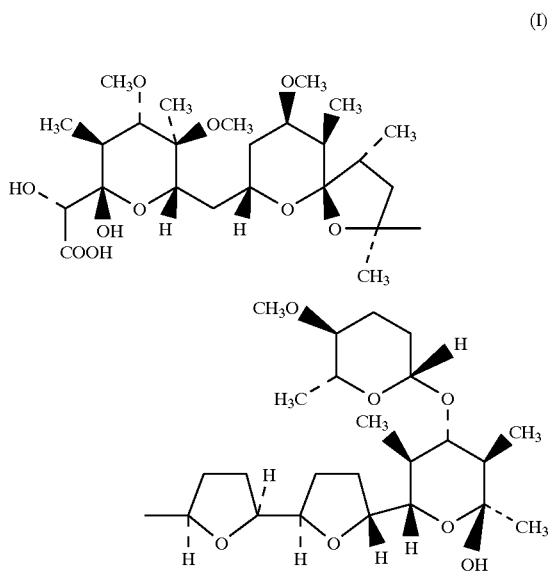

having absolute stereochemistry as shown; pharmaceutically acceptable cationic salts thereof; nutrient feed compositions comprising said antibiotic for poultry, cattle or swine; its use as an anticoccidial agent in poultry, in the treatment or prevention of swine dysentery, as a growth promotant in cattle or swine or as an anthelmintic in commercially important mammals, including dogs, cats, sheep, cattle and swine; a fermentation method for its preparation; and the Streptomyces sp. microorganism which produces said antibiotic in said fermentation method.

The compound (I) is a new member of the acidic polycyclic ether group of antibiotics. This family includes such well known agents as monensin (The Merck Index, 10th Ed., Merck and Co.,Inc., Rahway, N.J., 1983, monograph no. 6100), nigericin (loc. cit., monograph no. 6390), narasin (loc. cit., monograph no. 6271), lasalocid (loc. cit., monograph no. 5204), and salinomycin (loc. cit., monograph no. 8193). The subject has been reviewed by Westley, "Polyether Antibiotics", Adv. Appl. Microbiol., vol. 22, pp. 177–223 (1977). These compounds are generally known as coccidiostats, as feed additive-growth promotants, and/or as agents useful against swine dysentery.

SUMMARY OF THE INVENTION

A culture of Streptomyces sp., ATCC 55028, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said Streptomyces sp. ATCC 55028 in an aqueous nutrient medium comprising an assimilable source of carbon and nitrogen until a recoverable amount of said compound of the formula (I) is formed, preferably under submerged aerobic conditions. For use as an anthelmintic agent, an anticoccidial agent, in the prevention or treatment of swine dysentery, and/or as a growth promotant, the compound (I) is not necessarily separated from the fermentation and isolated in substantially pure form, but is alternatively used in crude form, either in precipitated form admixed with mycelium (recovered by filtration of the fermentation medium), or in solids obtained by spray- or freeze-drying the entire fermentation medium.

Said pharmaceutically-acceptable cationic salts include, but are not limited to, those of sodium, potassium, calcium, ammonia, N,N'-dibenzylethylene-diamine, N-methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote growth and/or improve the feed utilization of said cattle or swine, or to prevent or treat dysentery in swine; and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; to a method for preventing or treating dysentery in swine which comprises administering to said swine a compound of the formula (I) in an amount effective in preventing or treating said dysentery in said swine; to a method for controlling coccidial infections in poultry which comprises administering to said poultry an anticoccidially effective amount of the compound of the formula (I), particularly in the form of a nutrient feed composition; and to a method of controlling helminth infections in mammals (particularly dogs, cats, sheep, cattle and swine) which comprises administering to said mammal an anthelmintic effective amount of the compound of the formula (I).

Finally, the present invention is directed to a biologically pure culture of Streptomyces sp. ATCC 55028, said culture being capable of producing the compound of the formula (I) in a recoverable quantity upon fermentation in an aqueous nutrient medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated Streptomyces sp., and has been deposited under the Budapest treaty in The American Type Culture Collection, Rockville, Md. as the type culture under their accession number ATCC 55028. Permanency of the deposit of this culture at The American Type Culture Collection at Rockville, Md. and ready accessibility thereto by the public are afforded throughout the effective life of the patent.

This novel culture was derived from a soil sample collected in Kurashiki City, Okayama Prefecture, Japan; and identified in the culture collections of Pfizer Inc. as N840–52 and as F.D. 289200. Its description and classification were provided by Dr. L. H. Huang. This culture was found to produce narrow dimensions of the hyphae typical of the Actinomycetales, an aerial mycelium upon which spore chains are produced, and an unfragmented substrate mycelium. The results of the whole cell analyses further indicate that it belongs to the genus Streptomyces.

A slant culture of the microorganism on ATCC 172 media was inoculated into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the results read at varying times, but most commonly at fourteen days. The colors were described in common terminology, but exact colors were determined by comparisons with color chips from *The Color Harmony Manual*, fourth edition. The methods of whole-cell amino acid and sugar analyses are those described in Becker et al., Appl. Microbiol., vol. 12, pp. 421–423 (1964), and in Lechevalier, J. Lab. Clin. Med., Vol. 71, pp. 934–944 (1968), respectively. The type strain of *Streptomyces flocculus* ATCC 25453 was used for comparison purposes.

The culture was identified as follows:

Yeast Extract-Malt Extract Agar (ISP #2 medium, Difco)—Growth good; white to yellowish brown (3 le); moderately raised, wrinkled; aerial mycelium white; reverse yellowish brown (3 ne, 3 le); soluble pigment yellowish brown (3 ne).

Oatmeal Agar (ISP #3 medium, Difco)—Growth moderate, white to cream (near 2 ca); slightly raised, smooth, with white aerial mycelium; reverse cream to pale yellowish orange (2 ca, 3 ca); soluble pigment cream (2 ca).

Inorganic Salts-Starch Agar (ISP #4 medium, Difco)—Growth moderate to good; pink-gray (near gray series 5 dc, 5 fe); slightly to moderately raised, smooth to wrinkled, with white aerial mycelium; reverse yellowish brown, brown to reddish brown (3 le, 4 le, 4 ng, 5 ng); no soluble pigment.

Glycerol-Asparagine Agar (ISP #5 medium, Difco)—Growth poor; pale gray (near gray series 3 cb, 3 dc); thin, smooth to granular; aerial mycelium pale gray (near gray series 3 cb, 3 dc); reverse colorless, pale yellowish to yellowish brown (2 ea, 3 ic); no soluble pigment.

Czapek-Sucrose Agar (Waksman, "The Actinomycetes", v. 2, medium #1, p. 328, 1961)—Growth moderate; cream to pale gray (2 ca, near gray series 3 cb); slightly raised, smooth; aerial mycelium white to pale gray (near gray series 3 cb); reverse cream (2 ca); no soluble pigment.

Glucose-Asparagine Agar (ibid., medium #2)—Growth moderate; cream, white-red to red (2 ca, 6 gc, 6 le); slightly to moderately raised, smooth to wrinkled; aerial mycelium white; reverse same as surface; no soluble pigment.

Gordon and Smith's Tyrosine Agar (Gordon and Smith, J. Bacteriol., 69:147–150, 1955)—Growth good; white to cream (2 ca); slightly raised, smooth, with white aerial mycelium; reverse cream (2 ca); no soluble pigment.

Calcium Malate Agar (Waksman, Bacteriol. Rev., 21, 1–29, 1957)—Growth poor; cream (2 ca); thin, smooth, with white aerial mycelium; reverse colorless to cream (2 ca); no soluble pigment.

Casein Agar (Gordon and Smith, ibid.)—Growth good; cream, white-red to red (2 ca, 6½ gc, 7 ie, 6½ ic); raised, wrinkled, with no aerial mycelium; reverse cream to red (2 ca, 7 ic, 7 ie, 6½ le); soluble pigment white-red (6½ gc).

Bennett's Agar (Waksman, loc. cit., medium #30, p. 331)—Growth good; white, cream to brown (2 ca, 4 ie); raised, wrinkled; aerial mycelium white to cream (2 ca); reverse yellowish brown to red-brown (3 ne, 3 le, 4 ie); soluble pigment yellowish (2 ga).

Emerson's Agar (ibid., medium #28, p. 331)—Growth good; white to yellowish brown (3 ne, 3 le); raised, wrinkled; aerial mycelium white; reverse yellowish brown (3 ne, 3 le); soluble pigment yellowish brown (3 lc).

Nutrient Agar (ibid., medium #14, p. 330)—Growth moderate; white; slightly raised, smooth, with white aerial mycelium; reverse cream (2 ca); no soluble pigment.

Gelatin Agar (Gordon and Mihm, J. Bacteriol., 73, 15–27, 1957)—Growth good; white; moderately raised, wrinkled, with white aerial mycelium; reverse yellowish (near 2 ic); no soluble pigment.

Starch Agar (ibid.)—Growth good; white to cream (2 ca); moderately raised, wrinkled, with white aerial mycelium; reverse yellowish (2 ic); no soluble pigment.

Potato Carrot Agar (Lechevalier, Lab. Clin. Med., 71, 934–944, 1968, but use only 30 g. potatoes, 2.5 g. carrots and 20 g. agar)—Growth poor to moderate; white to cream (2 ca); slightly raised, smooth; with white aerial mycelium; reverse cream (2 ca); no soluble pigment.

Tap Water Agar (2%)—Growth poor; cream (2 ca); thin, smooth; aerial mycelium sparse, white; reverse colorless to cream (2 ca); no soluble pigment.

Morphological Properties—The morphological properties were observed after two weeks of incubation on Bennett's agar: spore mass in white or yellow color-series; spore chains in Section Spirales, tightly coiled or coiled into an irregular mass, each spore chain with 3 to 6 coils which were of small diameter; 6 to 25 spores per spore chain; sporophores monopodially branched, sometimes verticillately branched, often closely borne together forming clusters of spore masses; spores globose, oval to elliptical, 0.8–1.0 micron diameter or 1.2–1.7×0.8–1.0 microns; spores smooth, as revealed by scanning electron microscopy.

Biochemical Properties—Melanin not produced; hydrogen sulfide not produced; gelatin liquefied; starch hydrolyzed; nitrate not reduced to nitrite; growth on Jensen's cellulose broth but no growth on Levine and Schoenlein's cellulose broth; no decomposition on either cellulose broth; clearing and coagulation of milk; casein digestion negative; tyrosine digestion positive; calcium malate digestion negative. Carbohydrate utilization: glucose, sucrose, inositol, arabinose, fructose, mannitol, raffinose, rhamnose, and xylose all utilized.

| Temperature Relations | | | |
|---|---|---|---|
| 21° C. | 28° C. | 37° C. | 45° C. |
| Good Growth | Good to Excellent Growth | Good Growth | Poor Growth |

Cell Wall Analysis—The whole-cell hydrolysates contained LL-diaminopimelic acid, glucose, and ribose.

The present culture is characterized by the white or yellow spores in mass, the negative melanin reaction, the spiral spore chains, and the smooth spores. The whole-cell hydrolysates indicate the presence of LL-diaminopimelic acid, glucose, and ribose. Glucose, arabinose, fructose, inositol, mannitol, raffinose, rhamnose, sucrose, and xylose were all utilized. Thus, the culture belongs to the genus Streptomyces.

When compared with the known species of Streptomyces, the present culture closely resembles *S. herbescens*

(Krasil'nikov & Egorova) Pridham, S. sclerotialus Pridham, and S. flocculus (Duche) Waksman & Henrici in cultural, morphological and biochemical properties. However, it differs from S. herbescens in the absence of a green vegetative mycelium on some media.

The present culture differs from S. sclerotialus in the absence of sclelrotia and in the color of the vegetative mycelium. For example, on inorganic salts-starch agar and glucose-asparagine agar, the vegetative mycelium of the former is brown to red-brown and white-red to red, respectively, but that of the latter is light gray-yellow to light yellow-brown and cinnamon yellow, respectively.

When the present culture was compared with S. flocculus ATCC 25453, minor differences were noted. The present culture but not S. flocculus hydrolized starch and utilized rhamnose. S. flocculus but not the present culture produced hydrogen sulfide and reduced nitrate to nitrite. In addition to the colors of the vegetative mycelia shared in common by both cultures, those of the present culture may be pale yellow-orange on oatmeal agar, red-brown on inorganic salts-starch agar, and red on glucose-asparagine agar and casein agar.

On the basis of the data presented above, the present culture N840–52 is considered as a new strain of the genus Streptomyces and designated Streptomyces sp. It has been deposited at the American Type Culture Collection under the accession number ATCC 55028.

The antibiotic compound (I) of the present invention is readily produced by the present Streptomyces sp. by growing at from about 24° to about 36° C. under submerged conditions with agitation and aeration on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc. and calcium carbonate or phosphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, an inoculum is first prepared by scraping vegetative cells, growing on a suitable media, from slants or Roux bottles which have been inoculated with Streptomyces sp. ATCC 55028. The resulting vegetative cells are in turn used to inoculate shake flasks or inoculum tanks, also containing suitable growth media. Alternatively, the inoculum tanks are inoculated from the shake flasks. Following a suitable growth period (generally 120 to 144 hours in shake flasks and 168 to 196 hours in inoculum tanks), a fermenter, also containing suitable growth media, is inoculated under aseptic conditions with vegetative broth from the shake flasks or inoculum tanks. Upon completion of growth (generally about 120–196 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, Acta. Pathologica et Microbiologia Scandinav, Supp. 217, Section B: 64–68 [1971]), and employs brain heart infusion (BHI) agar and an inocula replicating device. Overnight growth tubes are diluted 100 fold for use as the standard inoculum (20,000–100,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Like other polycyclic ether antibiotics, the present compound of the formula (I) typically shows Gram positive antibacterial activity, as well as activity against Treponema hyodysenteriae (the causative agent of swine dysentery).

Efficacy data for the compound of the formula (I) and its salts against coccidial infections in chickens is obtained by the following method. Groups of 3–5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3–5 ten-day old chicks are fed a similar mash diet without compound (I) or its salts. They are also infected after 24 hours and serve as infected controls. Yet another group of 3–5 ten-day old chicks are fed the same mash diet without antibiotic and are not infected with coccidia. These served as normal controls. The results of treatment are evaluated after five days in the case of E. acervulina, and six days for all other challenges.

The criteria used to measure anticoccidial activity consists of lesion scores of 0 to 4 for E. tenella after J. E. Lynch, "A New Method of the Primary Evaluation of Anticoccidial Activity", Am. J. Vet. Res., 22, 324–326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", Exp. Parasit., 28, 30–36, 1970. Activity is measured by dividing the lesion score of each treated group by the lesion score of the infected control. In this test, the compound (I) and its cationic salts exhibit activity against Eimeria tenella, E. acervulina, E. maxima, and E. necatrix infections in poultry when incorporated into the mash diet of chickens at levels of about 2.0 to 50 ppm.

The present compound of the formula (I) is also generally useful in combination with certain other known anticoccidial agents, such as nicarbazin, 4,4'-dinitrocarbanilide or a naphthalenamine, as defined by Hamill et al., U.S. Pat. No. 4,582,822.

The anthelmintic activity of the compound of the formula (I) is evaluated against Caenorhabditis elegans using the in vitro screening test described by K. G. Simpkin and G. L. Coles in Parasitology, v. 79, p. 19 (1979). In this test, the compound of the formula (I), as its sodium salt, killed 100% of the worms at a well concentration of 50 ppm.

The insecticidal activity of the compound of the formula (I) the larval stage of the blowfly Lucilia cuprina (Q strain)

is demonstrated using a standard procedure in which first instar larvae are kept in contact with filter paper treated with test compound. The test compound is first applied to the paper as an acetone solution. The treated filter papers are then placed into tubes containing 1 ml of newborn calf serum and the first instars are added. The compound of the formula (I), in the form of its sodium salt, killed 100% of the larvae when applied to the filter paper at a level of 50 milligrams per square meter.

For the prevention or control of coccidiosis in poultry, the compound of this invention is orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid concentrate, or added directly to the feed as such, or in the form of a premix or concentrate. A premix or concentrate of therapeutic agent in a carrier is commonly employed for the inclusion of the agent in the feed. The therapeutic agent can be in substantially pure form (e.g., the free acid, or a pharmaceutically-acceptable salt thereof), in assayed crude form such as wet or dry mycelium or dried whole broth. Suitable carriers are liquid or solid, as desired, such as water, various meals (for example, soybean oil meal, linseed oil meal, corncob meal) and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements are added directly to the poultry feed to produce a nutritionally balanced, finished feed containing a therapeutically effective level of one or more of the compounds of this invention. The mixtures are thoroughly blended by standard procedures, such as in a twin shell blender, to ensure homogeneity.

For use in poultry, the use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of about 2.0 to 50 ppm. When administered in drinking water, the level which will be that which will provide the same daily dose of medication factored by the weight ratio of the average daily consumption of feed to the average daily consumption of water.

The activity of the compound of the formula (I) and its salts in the promotion of growth and/or increasing the efficiency of food utilization in swine or cattle can be measured directly by feeding test groups of animals various levels of the compound (I) or a salt in feed. Alternatively, British Patent Specification No. 1,197,826 details an in vitro rumen method for the evaluation of antibiotics in feeds.

For use in the prevention or treatment of swine dysentery, or in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I) in cattle or swine feed will generally be in the range of about 0.5 to 50 ppm. In ruminants the compound of the formula (I) can also be orally administered in the form of a bolus which is retained in the rumenoreticular sac, releasing the therapeutic agent at a substantially constant rate over a prolonged period of time, e.g., 4–8 weeks, providing a dose equivalent to that of the above daily dose in feed, i.e.:

average daily dose in milligrams =

(0.5 to 50) ppm × average daily feed consumption in Kg.

Exemplary of such a controlled release bolus is that of Cardinal, U.S. Pat. No. 4,601,893.

For use as an anthelmintic the compound of the formula (I) is administered as a formulation appropriate to the particular host animal and the specific helminth disease requiring treatment. Thus the compound is administered orally in the form of a conventional capsule, tablet, bolus or liquid drench; or administered subcutaneously or intramuscularly in the form of a conventional sterile solution or emulsion. Generally, for acute treatment of a helminth infection, the dosage will be in the range of 5–50 mg/Kg of animal body weight/day, dosed over a period of from 1–5 days, regardless of the route of administration.

For use as an insecticide and for treating agricultural pests the compound is applied as sprays, dusts, pour-on formulations, emulsions and the like in accordance with standard agricultural practice.

The present invention is illustrated by the following examples. However, it should be understood that the invention is not limited to the specific details of these examples.

EXAMPLE 1

Fermentation of Streptomyces sp. ATCC 55028
Isolation of the Antibiotic of the Formula (I) as Sodium Salt The Streptomyces sp. was initially grown by inoculating solid media on slants or Roux bottles with the ATCC 55028 culture, using ATCC medium No. 172, prepared and having composition as follows.

|  | Grams/liter |
|---|---|
| Glucose | 10 |
| Soluble Starch | 20 |
| Yeast Extract | 5 |
| Casein Enzymatic Hydrolysate | 5 |
| Calcium Carbonate | 1 |
| Distilled Water to 1000 ml; pH to 7.0 with KOH; Add Agar | 20 |

Meanwhile, 300 ml shake flasks were prepared using in each flask 100 ml of one or the other of the following media:

| C' | Grams/liter | JDYTT | Grams/liter |
| --- | --- | --- | --- |
| Cerelose | 10 | Cerelose | 10 |
| Soy Flour | 10 | Corn Starch | 5 |
| Corn Fermentation Solids | 5 | Corn Steep Liquor | 5 |
| Corn Starch | 10 | Casein Enzymatic Hydrolysate | 5 |
| Sodium Chloride | 5 | Cobalt Chloride | 0.002 |
| Cobalt Chloride | 0.002 | Calcium Carbonate | 3 |
| Calcium Carbonate | 1 | | |

The medium-containing shake flasks were then sterilized at 120° C. and 15 p.s.i. for 30 minutes. After cooling, the medium was inoculated with a vegetative cell suspension scraped from the above Streptomyces sp. slant culture. The flasks were shaken at 28° C. on a shaker having a displacement of 1.5 to 2.5 inches at 150 to 200 cycles per minute (CPM) for four to five days.

Meanwhile, 5 liter fermentation vessels were prepared containing 3 liters of one of the above C' or JDYTT media or the following media:

| UK1-2 | Grams/liter |
| --- | --- |
| Cerelose | 45 |
| Soy Flour | 10 |
| Corn Steep Liquor | 10 |
| Cobalt Chloride | 0.002 |
| Magnesium Sulfate | 0.10 |
| Calcium Carbonate | 3 |
| Manganese Sulfate | 0.10 |
| Ferric Sulfate | 0.10 |

An antifoaming agent (polypropyleneglycol, P2000, containing 10% ethylene oxide by weight, 1 ml) was added, and the vessels were sealed and sterilized at 120° C. and 15 p.s.i. for 45 minutes. The vessels were then inoculated with one shake flask (ca 3% inoculum), and fermented for 120 to 168 hours at 30° C., stirring at 1700 revolutions per minute (RPM) with an air rate of one volume of air per volume of liquid per minute.

When the fermentation was completed (based on an antibiotic disc assay versus *B. subtilis* ATCC 6633) the fermenters were stopped and filtered at the natural pH with the aid of a diatomaceous earth. The filter cake was slurried in methanol, concentrated in vacuo, diluted with 2–3 volumes of water then extracted 2x with ⅓ to ½ volume of either methylisobutyl ketone or n-butanol. The solvent layer was separated from the aqueous phase by aspiration or centrifugation, sparkled and concentrated in vacuo to yield the antibiotic of the formula (I) in crude form as a viscous oil.

The bioactivity of the broth and subsequent recovery streams can be followed by using a sensitive strain of *Bacillus subtilis* ATCC 6633 or *Staphylococcus aureus* ATCC 6538. The components in the broth and recovery streams can be visualized by thin layer chromatography (tlc) using Analtech silica gel GF plates employing ethyl acetate as eluant. The developed plates are sprayed with vanillin reagent (3 g vanillin in 75 ml ethanol and 25 ml 85% phosphoric acid) and heated to 80° C. The antibiotic product of the formula (I) appears as a deep wine-red colored spot. The developed tlc plate can also be overlayed with agar seeded with either *S. aureus* or *B. subtilis* to which 2,3,5-triphenyl-2H-tetrazolium chloride monohydrate has been added and incubated at 37° C. for 16 hours to visualize the antibiotic (white spots against a pink background).

Scale-up in large fermentation vessels was carried out by preparing shake flasks containing 0.7 liters of C' or JDYTT medium. The shake flask inoculum was fermented for 5 to 7 days at 28° C., and used to inoculate a 200 liter fermentation vessel containing 100 liters of JDYTT medium, respectively. The fermentation, after proceeding for 7 to 10 days, was harvested. The whole broth was extracted with 33 liters of methylisobutyl ketone at natural pH. The organic extract was separated on an alpha-DeLaval separator and concentrated under vacuum to yield the crude antibiotic of the formula I as an oil. The oil was taken up in ethyl acetate, treated with activated carbon to remove highly colored impurities, restripped to an oil, and chromatographed on silica gel gradiently eluted with $CH_2Cl_2$/ethyl acetate. Initial fractions eluted with $CH_2Cl_2$ were discarded. Product containing fractions, eluted with 3:1 to 3:2 $CH_2Cl_2$:ethyl acetate were combined, treated with additional activated carbon and stripped to yield crude antibiotic of the formula (I). The crude was taken up in chloroform, extracted with dilute phosphoric acid and then with pH 9.0 phosphate buffer. The organic phase was dried ($Na_2SO_4$), stripped, and the residue crystallized from hexane and dried under high vacuum to yield 4.1 g of the antibiotic of the formula (I) in the form of its sodium salt; m.p. 193–195° C.; $[alpha]_D^{25}=-9.7°$ (c=1, $CH_3OH$).

Analysis calculated for $C_{47}H_{79}O_{17}Na$:

C, 60.09; H, 8.48%.

Found: C, 59.81; H, 8.63%.

$^{13}C$-NMR($CDCl_3$)ppm (no. of attached H in parentheses): 179.7 (0), 108.3 (0), 103.0 (1), 99.7 (0), 98.9 (0), 86.3 (1), 85.5 (1), 83.0 (1), 82.9 (0), 80.9 (1), 80.5 (1), 80.2 (1), 79.9 (1), 79.5 (1), 78.7 (0), 74.7 (1), 74.6 (1), 72.4 (1), 67.6 (1), 61.7 (1), 60.8 (3), 59.3 (3), 56.2 (3), 50.9 (3), 48.2 (1), 41.0 (2), 39.7 (1), 39.7 (1), 39.4 (1), 37.0 (1), 33.2 (2), 31.3 (2), 30.9 (2), 29.1 (2), 28.5 (3), 27.3 (2), 27.1 (3), 24.2 (2), 24.2 (2), 22.8 (2), 18.8 (3), 13.9 (3), 13.2 (3), 13.2 (3), 12.6 (3), 12.5 (3), and 10.9 (3).

EXAMPLE 2

Compound (I) in the Free Acid Form

The free acid form of the antibiotic of the formula (I) was prepared by vigorously shaking a chloroform solution of the sodium salt with an equal volume of hydrochloric acid at pH 2 in a separatory funnel. The phases were separated, and the chloroform layer was washed with water and then evaporated under vacuum to give the free acid; m.p. 111–113° C.; $[alpha]_D^{25}=-6.8°$ (c=1, $CH_3OH$).

EXAMPLE 3

Compound (I) as Silver Salt for X-Ray Crystallography

The free acid form of the preceding Example (100 mg) was dissolved in 100 ml of $CHCl_3$. Silver acetate (150 mg in 100 ml of water) was added and the mixture vigorously shaken in a separatory funnel. The organic phase was separated, washed with water, and evaporated to afford present title product as a white solid. This was recrystallized by slow evaporation from CHCl$_3$/ether (1:1). A single crystal X-ray analysis by Dr. J. Bordner indicated that the antibiotic of the present invention was of the absolute stereochemical formula (I) as depicted above.

We claim:

1. A biologically pure culture of Streptomyces sp. ATCC 55028, said culture being capable of producing the compound having the formula

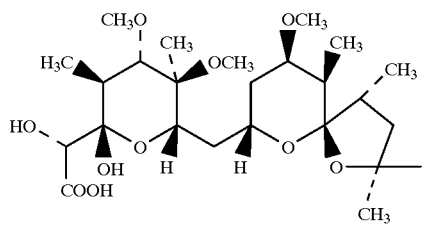

-continued

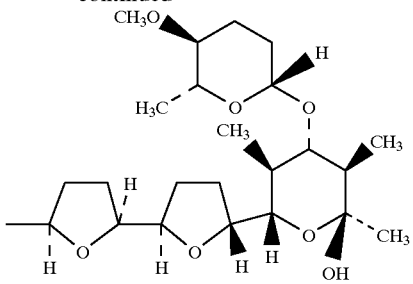

in a recoverable quantity upon fermentation in an aqueous nutrient medium comprising assimilable sources of carbon and nitrogen.

2. The culture of claim 1 in freeze-dried form.

* * * * *